United States Patent
Wang

(10) Patent No.: US 10,610,323 B2
(45) Date of Patent: Apr. 7, 2020

(54) TELESCOPING CONTROL MECHANISM FOR CONTROLLING A MEDICAL INSTRUMENT

(71) Applicant: HIWIN TECHNOLOGIES CORP., Taichung (TW)

(72) Inventor: Ren-Jeng Wang, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 323 days.

(21) Appl. No.: 15/066,149

(22) Filed: Mar. 10, 2016

(65) Prior Publication Data
US 2017/0258548 A1    Sep. 14, 2017

(51) Int. Cl.
*A61B 90/10* (2016.01)

(52) U.S. Cl.
CPC .................................. *A61B 90/10* (2016.02)

(58) Field of Classification Search
CPC ... A61B 90/10; A61B 34/00; A61B 90/00–98; A61B 2090/101; A61B 2090/103; A61B 34/35; A61B 34/37; A61B 34/70–72
See application file for complete search history.

(56) References Cited

U.S. PATENT DOCUMENTS

| 5,397,323 A | 3/1995 | Taylor et al. |
| 5,997,471 A | 12/1999 | Gumb et al. |
| 2010/0079099 A1* | 4/2010 | Katsuki ............. G05B 23/0256 318/565 |

FOREIGN PATENT DOCUMENTS

| DE | 102013002818 A1 | 8/2014 |
| DE | 202014104654 U1 | 11/2014 |
| EP | 2446807 A1 | 2/2012 |
| JP | 2014-061327 A | 4/2014 |
| JP | 2014-095953 A | 5/2014 |
| JP | 2014095953 A * | 5/2014 ......... A61B 1/00149 |

* cited by examiner

*Primary Examiner* — Kathleen S Holwerda
*Assistant Examiner* — Brooke Labranche
(74) *Attorney, Agent, or Firm* — Wang Law Firm, Inc.

(57) ABSTRACT

A telescoping control mechanism for controlling a medical instrument, the medical instrument includes a telescoping axis which intersects a patient at a work point, the telescoping control mechanism includes: a first rotary module disposed on a base, and including a first axis which extends through the work point; a second rotary module disposed on the base and including a second pivot which is pivoted to the base and has a second axis perpendicular to the first axis; a linkage module including a proximal linkage assembly disposed on the second pivot and parallel to the telescoping axis, and a distal linkage assembly for mounting of the medical instrument; and a telescoping module disposed on the proximal linkage assembly to drive the distal linkage assembly to reciprocate along the proximal linkage assembly, which consequently causes movements of the medical instrument along the telescoping axis.

4 Claims, 8 Drawing Sheets

TELESCOPING CONTROL MECHANISM FOR CONTROLLING A MEDICAL INSTRUMENT

BACKGROUND

Field of the Invention

The present invention relates to a control mechanism, and more particularly to a telescoping control mechanism for controlling a medical instrument.

Related Prior Art

MIS (minimally invasive surgery) has found wide application in surgical operations due to the advantages of small wounds, a quicker recovery time and shorter hospital stays. MIS is performed by remote-control manipulation of instruments (such as endoscope), so that the instrument can be moved stably in multiple axial directions.

As shown in FIG. 1, a remote center-of-motion robot for surgery disclosed in U.S. Pat. No. 5,397,323 comprises two parallel adjustable telescoping links 11, 12 which are connected to parallel links 13A, 13B, 13C by pivot joints 14, and further comprises actuators 15A and 15B, so that the instrument 16 can move in multiple axial directions to perform surgery or inspection.

The motion of the instrument 16 is generally controlled by the linear actuator 15A, and the linear actuator 15A is connected to the outer end 11A, 12A of the parallel adjustable telescoping links 11, 12, where is close to the instrument 16 and the work point P on the patient 17. Therefore, the surgical operation space is limited, which causes inconveniences to the surgeon, and is not conducive to performing of the MIS.

The present invention has arisen to mitigate and/or obviate the afore-described disadvantages.

SUMMARY

The present invention is aimed at providing a telescoping control mechanism for controlling a medical instrument, wherein no actuators are arranged close to the medical instrument and the work point. Therefore, the surgical operation space around the medical instrument and the work point on the patient is increased, which brings convenience to the surgeon, and is conducive to performing of the MIS.

Therefore, a telescoping control mechanism for controlling a medical instrument is provided by the present invention, the medical instrument includes a telescoping axis which passes through a work point, the telescoping control mechanism comprises:

a base; a first rotary module disposed on the base, and including a first axis which extends through the work point, the first rotary module driving the base to revolve about the first axis; a second rotary module disposed on the base, and including a second pivot which is pivoted to the base and has a second axis perpendicular to the first axis; a linkage module including a proximal linkage assembly and a distal linkage assembly which are assembled to each other, the distal linkage assembly is located closer to the work point than the proximal linkage assembly, the proximal linkage assembly being disposed on the second pivot of the second rotary module and parallel to the telescoping axis, the distal linkage assembly including a first distal rod which is movably disposed on the proximal linkage assembly, and a second distal rod which is located closer to the work point than the first distal rod and provided for mounting of the medical instrument; and a telescoping module disposed on the proximal linkage assembly, and being connected to and driving the distal linkage assembly to reciprocate on the proximal linkage assembly along the telescoping axis, so as to consequently cause movements of the medical instrument along the telescoping axis.

Preferably, the first rotary module includes a first motor, a first deceleration mechanism and a first belt, the first motor is fixed on the base and includes a first rotary shaft, the first deceleration mechanism is fixed on the base and includes a first input shaft and a first output shaft drivingly connected to the first input shaft, the first output shaft has an axis that is coaxial with the first axis, and the first belt is drivingly connected between the first rotary shaft and the first input shaft.

Preferably, the first output shaft is pivotally mounted on a base frame.

Preferably, the second rotary module includes a second motor, a second deceleration mechanism and a second belt, the second motor is fixed on the base and includes a second rotary shaft, the second deceleration mechanism is fixed on the base and includes a second input shaft and the second pivot which is drivingly connected to the second input shaft, the second belt is drivingly connected between the second rotary shaft and the second input shaft, the second motor rotates the second pivot to consequently cause repeated revolution motion of the linkage module, the telescoping module and the medical instrument about the second axis.

Preferably, the proximal linkage assembly includes a first proximal rail, a second proximal rail parallel to the first proximal rail, a connecting rod connected between the first and second proximal rails, a first slide block slidably mounted on the first proximal rail, and a second slide block slidably mounted on the second proximal rail, the first proximal rail includes a first proximal end fixed to the second pivot, the second proximal rail includes a second proximal end fixed to the base, the telescoping module includes a screw parallel to the second proximal rail, a nut screwed onto the screw and fixed to the second slide block, and a third motor which drives the screw to rotate, and the first distal rod of the distal linkage assembly of the linkage module is fixed both to the first slide block and the nut.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

DETAILED DESCRIPTION

Figure 1:
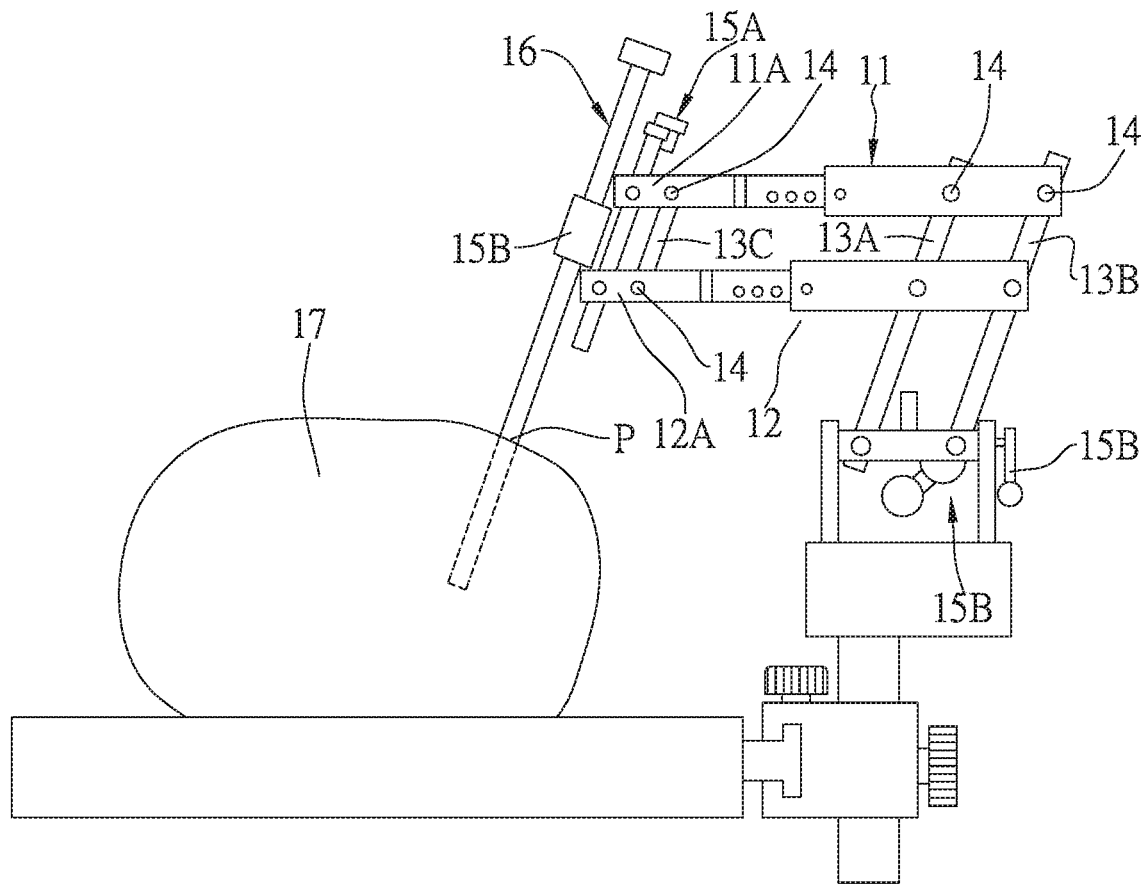
FIG. 1 shows a remote center-of-motion robot for surgery disclosed in U.S. Pat. No. 5,397,323.

The present invention will be clearer from the following description when viewed together with the accompanying drawings, which show, for purpose of illustrations only, the preferred embodiment in accordance with the present invention.

Referring to FIGS. 2-5, a telescoping control mechanism for controlling a medical instrument 91 in accordance with the preferred embodiment of the present invention is shown, wherein the medical instrument 91 includes a telescoping axis 911 along which the medical instrument 91 can perform telescoping movements. The telescoping axis 911 intersects the patient 92 at a work point P. The telescoping control mechanism comprises: a base 20, a first rotary module 30, a second rotary module 40, a linkage module 50 and a telescoping module 60.

The first rotary module 30 is disposed on the base 20, and includes a first axis 31 which extends through the work point P. The first rotary module 30 drives the base 20 to revolve about the first axis 31. In this embodiment, the first rotary module 30 includes a first motor 32, a first deceleration mechanism 33 and a first belt 34. The first motor 32 is fixed on the base 20 and includes a first rotary shaft 321. The first deceleration mechanism 33 is fixed on the base 20, and includes a first input shaft 331 and a first output shaft 332 drivingly connected to the first input shaft 331. The first output shaft 332 has an axis that is coaxial with the first axis 31. The first belt 34 is drivingly connected between the first rotary shaft 321 and the first input shaft 331. The first output shaft 332 is pivotally mounted on a base frame 96.

The second rotary module 40 is disposed on the base 20, and includes a second pivot 432 which is pivoted to the base 20 and has a second axis 41 perpendicular to the first axis 31. In this embodiment, the second rotary module 40 includes a second motor 42, a second deceleration mechanism 43 and a second belt 44. The second motor 42 is fixed on the base 20, and includes a second rotary shaft 421. The second deceleration mechanism 43 is fixed on the base 20, and includes a second input shaft 431 and the second pivot 432 which is drivingly connected to the second input shaft 431. The second belt 44 is drivingly connected between the second rotary shaft 421 and the second input shaft 431. The second motor 42 rotates the second pivot 432 to consequently cause repeated revolution motion of the linkage module 50, the telescoping module 60 and the medical instrument 91 about the second axis 41.

The linkage module 50 includes proximal linkage assembly 51 and a distal linkage assembly 52 which are assembled to each other. The distal linkage assembly 52 is located closer to the work point P than the proximal linkage assembly 51. The proximal linkage assembly 51 is disposed on the second pivot 432 of the second rotary module 40, and parallel to the telescoping axis 911. The distal linkage assembly 52 includes a first distal rod 521 which is movably disposed on the proximal linkage assembly 51 and capable of moving parallel to the telescoping axis 911, and a second distal rod 522 which is located closer to the work point P than the first distal rod 521 and provided for mounting of the medical instrument 91.

The telescoping module 60 is disposed on the proximal linkage assembly 51 and located farther away from work point P than the second distal rod 522 of the distal linkage assembly 52, and is connected to and drives the distal linkage assembly 52 to reciprocate on the proximal linkage assembly 51 along the telescoping axis 911, which consequently causes movements of the medical instrument 91 along the telescoping axis 911.

Figure 2:
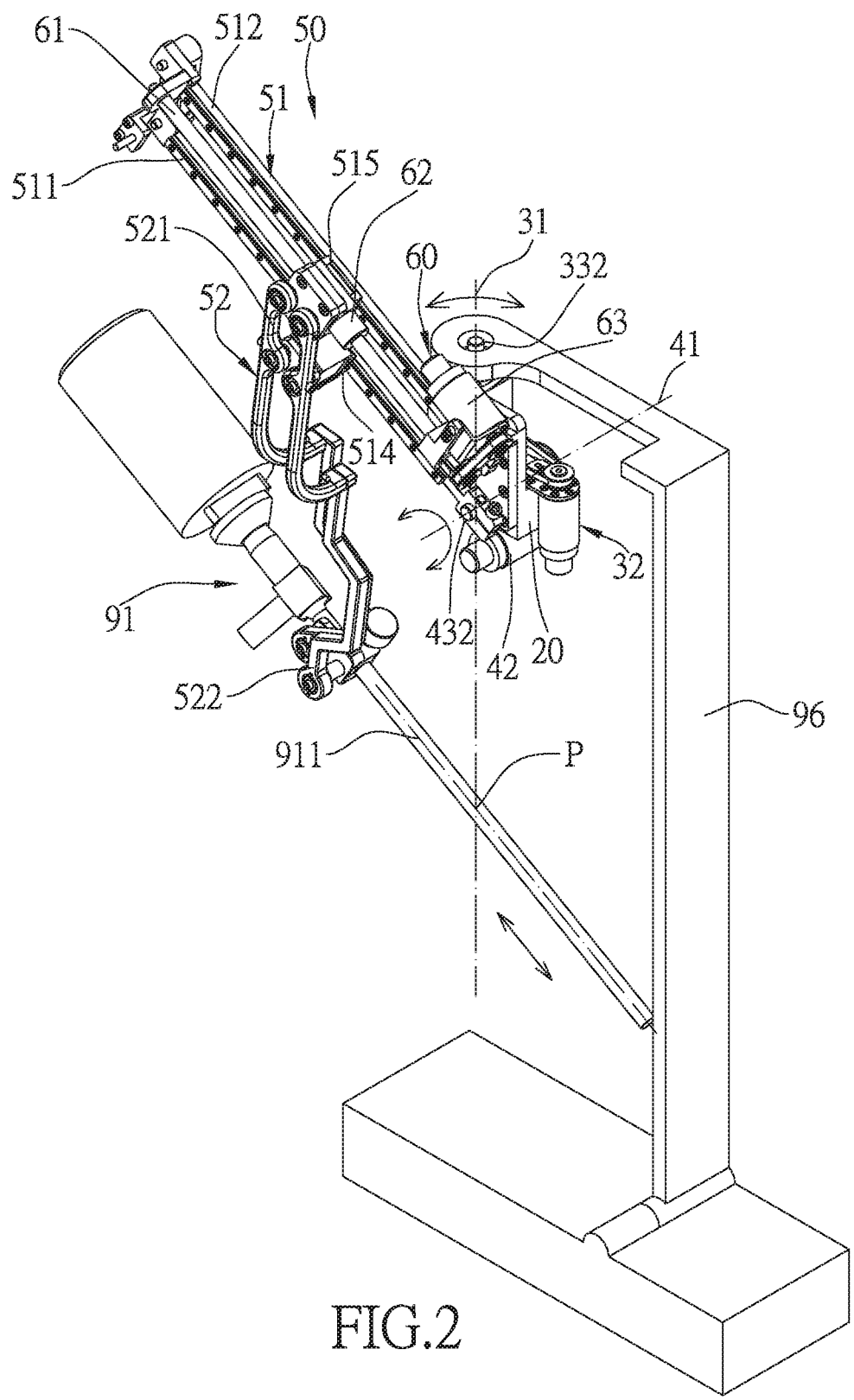
FIG. 2 is a perspective view of a telescoping control mechanism for controlling a medical instrument in accordance with the preferred embodiment of the present invention.
Figure 3:
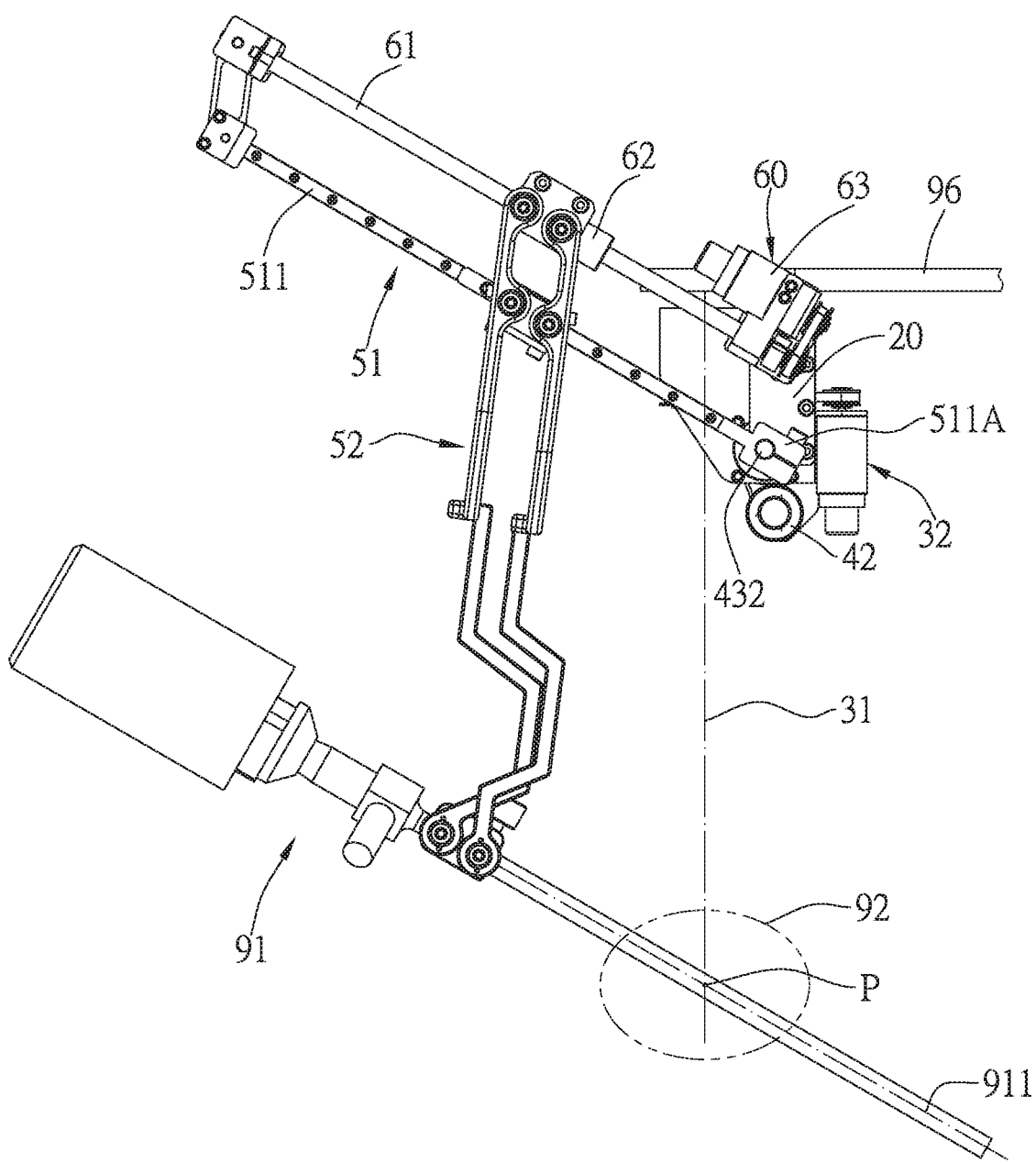
FIG. 3 is a front view of a part of the telescoping control mechanism for controlling a medical instrument in accordance with the preferred embodiment of the present invention.
Figure 4:
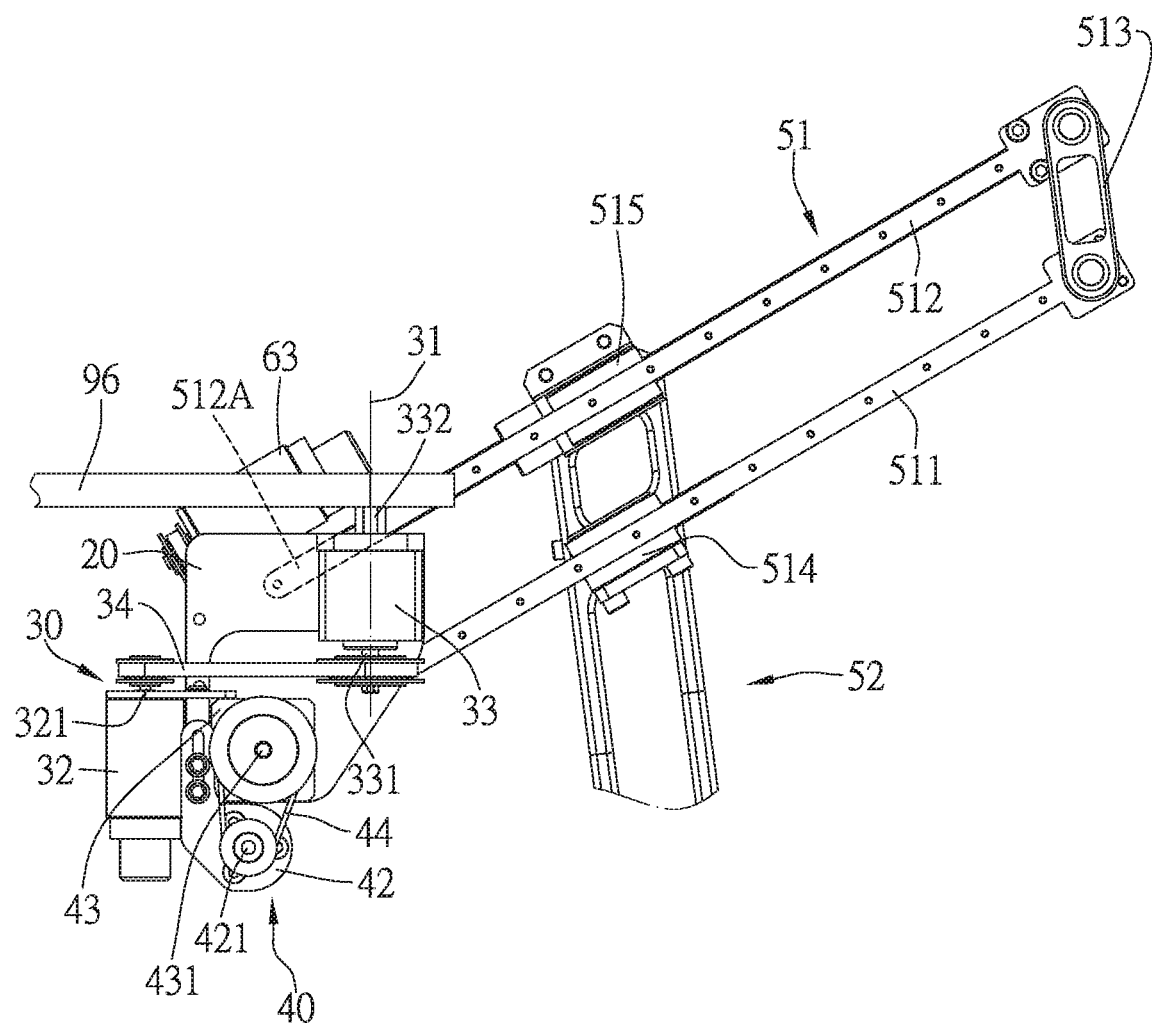
FIG. 4 is a rear view of a part of the telescoping control mechanism for controlling a medical instrument in accordance with the preferred embodiment of the present invention.
Figure 5:
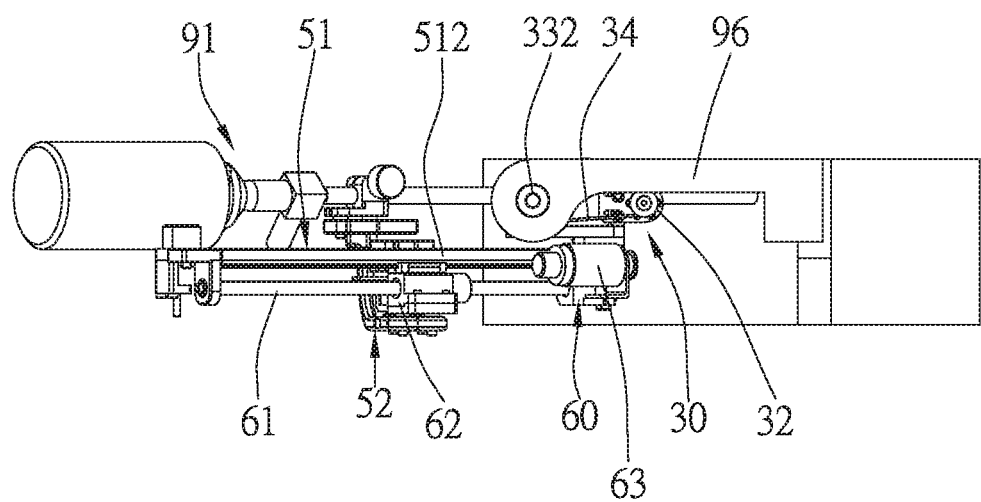
FIG. 5 is a top view of the telescoping control mechanism for controlling a medical instrument in accordance with the preferred embodiment of the present invention.
Figure 6:
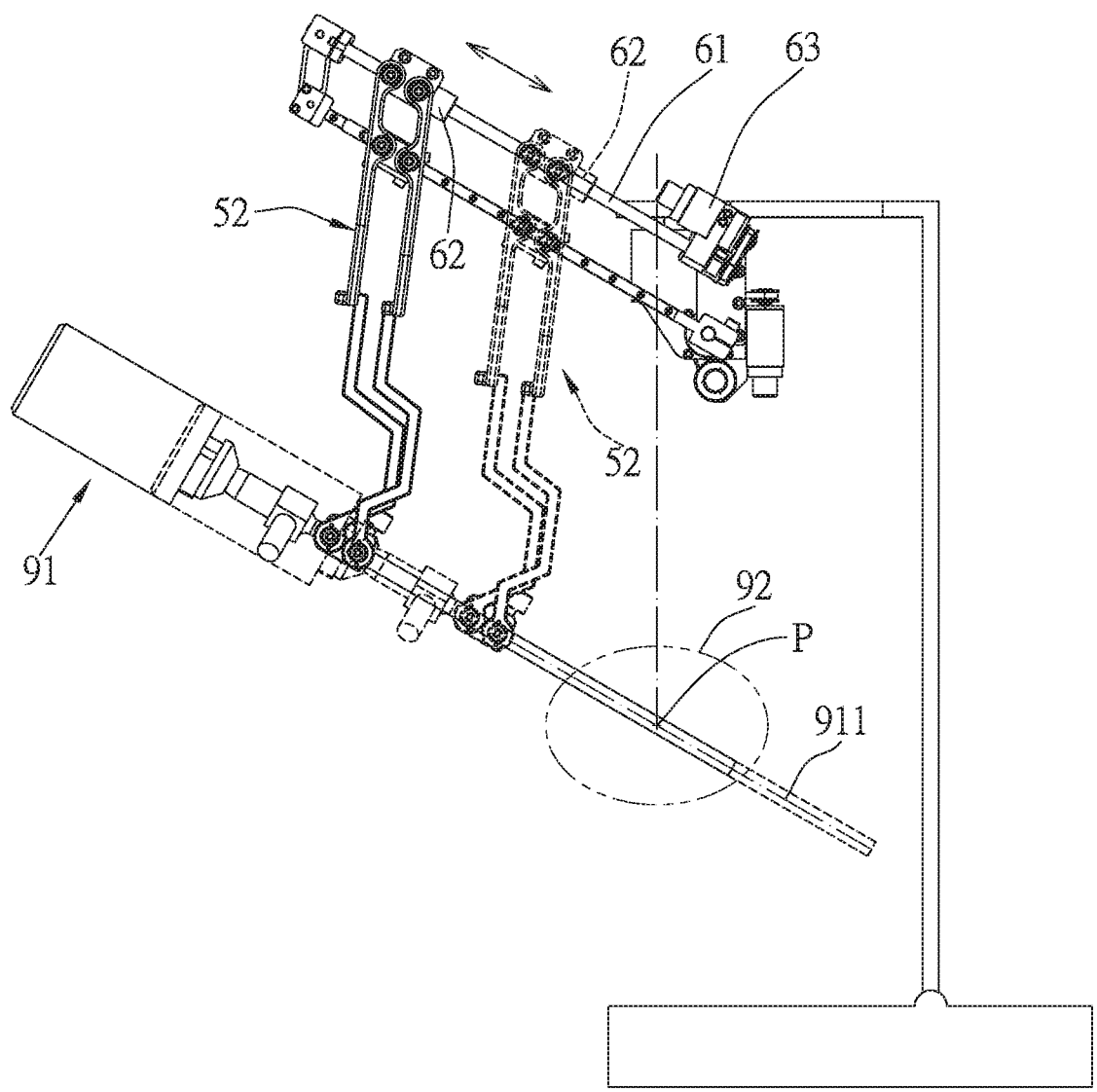
FIG. 6 is an illustrative view showing the telescoping motion of the medical instrument in accordance with the preferred embodiment of the present invention.
Figure 7:
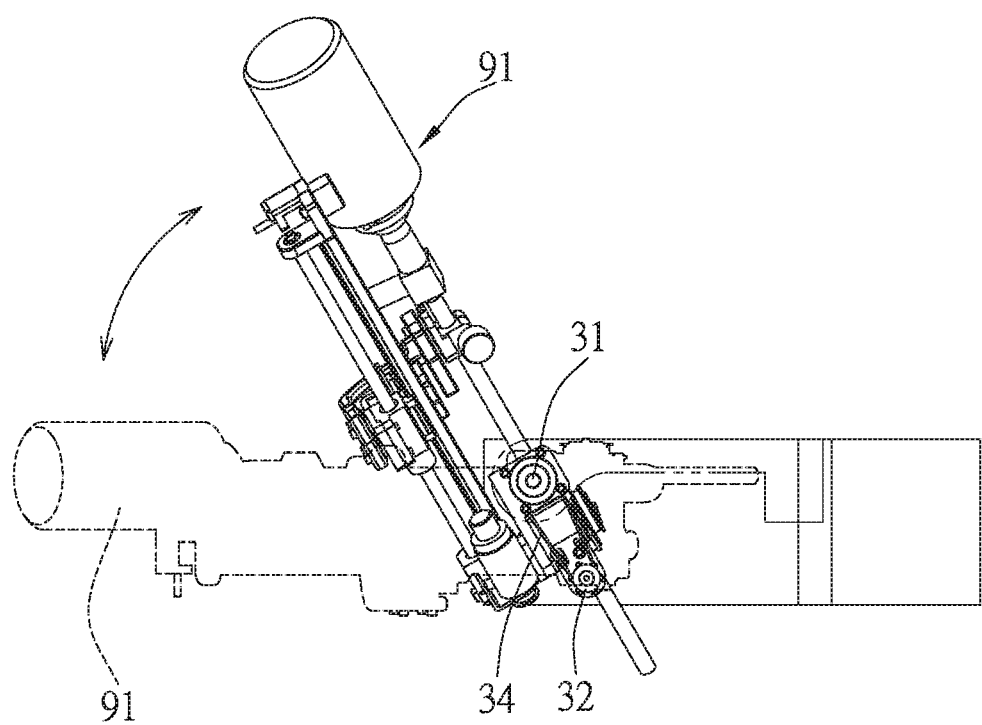
FIG. 7 is an illustrative view showing the first axis motion of the medical instrument in accordance with the preferred embodiment of the present invention.
Figure 8:
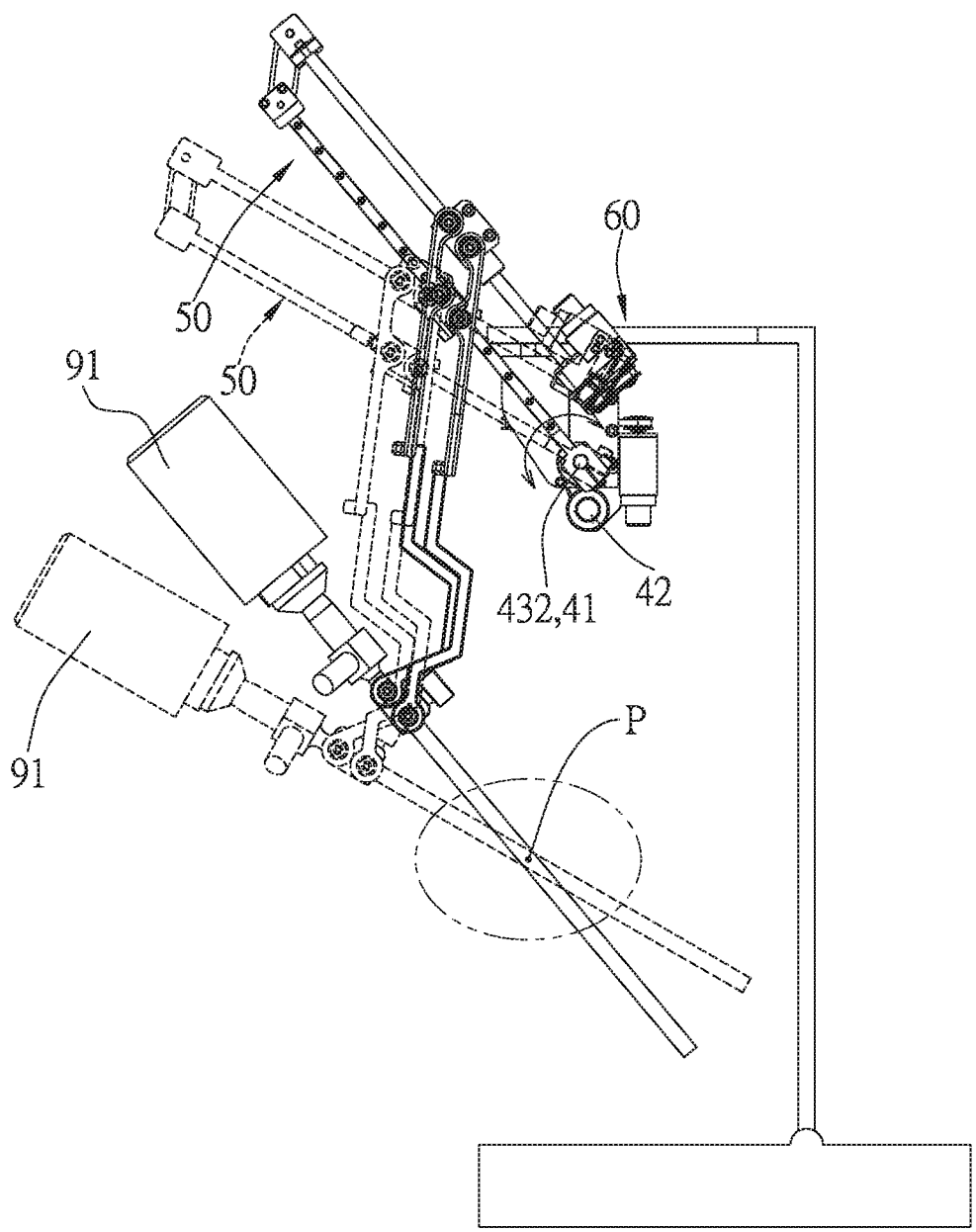
FIG. 8 is an illustrative view showing the second axis motion of the medical instrument in accordance with the preferred embodiment of the present invention.

In this embodiment, the proximal linkage assembly 51 includes a first proximal rail 511, a second proximal rail 512 parallel to the first proximal rail 511 and located farther away from the work point P than the first proximal rail 511, a connecting rod 513 connected between the first and second proximal rails 511, 512, a first slide block 514 slidably mounted on the first proximal rail 511, and a second slide block 515 slidably mounted on the second proximal rail 512. The first proximal rail 511 includes a first proximal end 511A fixed to the second pivot 432, and the second proximal rail 512 includes a second proximal end 512A fixed to the base 20. The distal linkage assembly 52 includes two rods. The telescoping module 60 includes a screw 61 which is mounted on the proximal linkage assembly 51 and parallel to the second proximal rail 512 and located farther away from the work point P than the second distal rod 522 of the distal linkage assembly 52, a nut 62 screwed onto the screw 61 and fixed to the second slide block 515, and a third motor 63 which is mounted on the proximal linkage assembly 51 and drives the screw 61 to rotate. The first distal rod 521 of the distal linkage assembly 52 of the linkage module 50 is fixed both to the first slide block 514 and the nut 62, which enables the telescoping module 60 to drive the distal linkage assembly 52 to move back and forth repeatedly along the proximal linkage assembly 51, consequently causing repeated movements of the medical instrument 91 along the telescoping axis 911. Just as shown in FIGS. 2, 3 and 6, the third motor 63 rotates the screw 61 to cause repeated back and forth movement of the nut 62 along the screw 61 (which is the same as the direction of the telescoping axis 911), so that the distal linkage assembly 52 and the medical instrument 91 which are fixed directly or indirectly to the nut 62 are caused to move back and forth along the telescoping axis 911.

With the structural design of the first rotary module 30, the second rotary module 40, the telescoping module 60 and the linkage module 50, the medical instrument 91, in addition to revolving about the first and second axes 31, 41 while being maintained at the work point P on the patient, is also allowed to move back and forth along the telescoping axis 911 passing through the work point P to perform surgery or inspection.

With arrangement of the proximal linkage assembly 51 and the distal linkage assembly 52, plus the driving of the telescoping module 60, the medical instrument 91 can move back and forth along the telescoping axis 911 passing through the work point P to perform surgery or inspection. In addition to that, the telescoping module 60 is disposed on the proximal linkage assembly 51, the first distal rod 521 of the distal linkage assembly 52 is movably disposed on the proximal linkage assembly 51, and the second distal rod 522 of the distal linkage assembly 52 is provided for mounting of the medical instrument 91, therefore, the telescoping module 60 for driving movements of the medical instrument 91 along the telescoping axis 911 is located at a position where is farther away from the medical instrument 91 and the work point P on the patient as well. Namely, no actuators are arranged close to the medical instrument 91 and the work point P. Therefore, the surgical operation space around the medical instrument 91 and the work point P on the patient is increased, which brings convenience to the surgeon, and is conducive to performing of the MIS.

The revolving motion of the medical instrument 91 about the first and second axes at the work point P is described as follows:

The first axis revolution: as shown in FIGS. 2, 4, 5 and 7, when the first motor 32 rotates the first input shaft 331 via the first belt 34 and the first deceleration mechanism 33, the first output shaft 332 rotates in a decelerated manner At this moment, the base 20, and the second rotary module 40, the linkage module 50 and the telescoping module 60 directly and indirectly mounted thereon will revolve about the first output shaft 332 and the first axis 31. Since the first axis 31 passes through the work point P, the medical instrument 91 is allowed to revolve an angle about the work point P to perform the first axis revolution.

The second axis revolution: as shown in FIGS. 2, 4, 5 and 8, when the second motor 42 rotates the second input shaft 431 via the second belt 44 and the second deceleration mechanism 43, the second pivot 432 rotates in a decelerated manner. At this moment, the linkage module 50 and the telescoping module 60 directly and indirectly mounted on the second pivot 432 will revolve about the second pivot 432 and the second axis 41. Since the second axis 41 is perpendicular to the first axis 31, and the first axis 31 passes through the work point P, the medical instrument 91 is allowed to revolve an angle about the work point P to perform the second axis revolution.

While we have shown and described various embodiments in accordance with the present invention, it is clear to those skilled in the art that further embodiments may be made without departing from the scope of the present invention.

What is claimed is:

1. A telescoping control mechanism for controlling a medical instrument, the medical instrument including a telescoping axis which passes through a work point, the telescoping control mechanism comprising:
    a base;
    a first rotary module disposed on the base, and including a first axis which extends through the work point, the first rotary module driving the base to revolve about the first axis;
    a second rotary module disposed on the base, and including a second pivot which is pivoted to the base and has a second axis perpendicular to the first axis;
    a linkage module including a proximal linkage assembly and a distal linkage assembly which are assembled to each other, the distal linkage assembly being located closer to the work point than the proximal linkage assembly, the proximal linkage assembly being disposed on the second pivot of the second rotary module and parallel to the telescoping axis, the distal linkage assembly including a first distal rod which is movably disposed on the proximal linkage assembly and capable of moving parallel to the telescoping axis, and a second distal rod which is located closer to the work point than the first distal rod and provided for mounting of the medical instrument; and
    a telescoping module disposed on the proximal linkage assembly and located farther away from the work point than the second distal rod of the distal linkage assembly, and being connected to and driving the distal linkage assembly to reciprocate on the proximal linkage assembly along the telescoping axis, so as to consequently cause movements of the medical instrument along the telescoping axis;
    wherein the proximal linkage assembly includes a first proximal rail, a second proximal rail parallel to the first proximal rail and located farther away from the work point than the first proximal rail, a connecting rod connected between the first and second proximal rails, a first slide block slidably mounted on the first proximal rail, and a second slide block slidably mounted on the second proximal rail, the first proximal rail includes a first proximal end fixed to the second pivot, the second proximal rail includes a second proximal end fixed to the base, the telescoping module includes a screw which is mounted on the proximal linkage assembly and parallel to the second proximal rail and located farther away from the work point than the second distal rod of the distal linkage assembly, a nut screwed onto the screw and fixed to the second slide block, and a third motor which is mounted on the proximal linkage assembly and drives the screw to rotate, and the first distal rod of the distal linkage assembly of the linkage module is fixed both to the first slide block and the nut.

2. The telescoping control mechanism as claimed in claim 1, wherein the first rotary module includes a first motor, a first deceleration mechanism and a first belt, the first motor is fixed on the base and includes a first rotary shaft, the first deceleration mechanism is fixed on the base and includes a first input shaft and a first output shaft drivingly connected to the first input shaft, the first output shaft has an axis that is coaxial with the first axis, and the first belt is drivingly connected between the first rotary shaft and the first input shaft.

3. The telescoping control mechanism as claimed in claim 2, wherein the first output shaft is pivotally mounted on a base frame.

4. The telescoping control mechanism as claimed in claim 1, wherein the second rotary module includes a second motor, a second deceleration mechanism and a second belt, the second motor is fixed on the base and includes a second rotary shaft, the second deceleration mechanism is fixed on the base and includes a second input shaft and the second pivot which is drivingly connected to the second input shaft, the second belt is drivingly connected between the second rotary shaft and the second input shaft, the second motor rotates the second pivot to consequently cause repeated revolution motion of the linkage module, the telescoping module and the medical instrument about the second axis.

* * * * *